United States Patent [19]
O'Neill et al.

[11] Patent Number: 5,993,623
[45] Date of Patent: Nov. 30, 1999

[54] SOLID ELECTROLYTE GAS ANALYZER WITH IMPROVED CIRCUIT AND HOUSING CONFIGURATION

[75] Inventors: Michael G. O'Neill; Joel P. Muzzy, both of Wooster; Michael T. Estvander, Wadsworth, all of Ohio

[73] Assignee: Rosemount Analytical Inc., Orrville, Ohio

[21] Appl. No.: 08/719,127

[22] Filed: Sep. 24, 1996

[51] Int. Cl.$^6$ .................................................. G01N 27/407
[52] U.S. Cl. .......................... 204/424; 204/406; 204/408
[58] Field of Search .................................. 204/408, 406, 204/421–429

[56] References Cited

U.S. PATENT DOCUMENTS

| | | | |
|---|---|---|---|
| 3,400,054 | 9/1968 | Ruka et al. | 204/1 |
| 3,661,748 | 5/1972 | Blackmer | 204/195 |
| 3,684,924 | 8/1972 | Miller, Jr. | 317/18 B |
| 3,915,828 | 10/1975 | Cleary et al. | 204/195 S |
| 3,928,161 | 12/1975 | McIntyre et al. | 204/195 |
| 4,279,142 | 7/1981 | McIntyre | 73/1 G |
| 4,280,505 | 7/1981 | Dali et al. | 204/415 |
| 4,365,604 | 12/1982 | Sone | 204/424 |
| 4,376,026 | 3/1983 | Hoffman et al. | 204/195 |
| 4,383,907 | 5/1983 | Legrand et al. | 204/426 |
| 4,415,878 | 11/1983 | Novak | 338/34 |
| 4,462,872 | 7/1984 | Nelson | 204/1 T |
| 4,554,439 | 11/1985 | Cross et al. | 219/497 |
| 4,604,517 | 8/1986 | Barry | 219/494 |
| 5,137,616 | 8/1992 | Poor et al. | 204/428 |
| 5,329,806 | 7/1994 | McClanahan et al. | 73/31.05 |
| 5,353,200 | 10/1994 | Bodin et al. | 361/816 |
| 5,429,737 | 7/1995 | Pribat et al. | 204/426 |

FOREIGN PATENT DOCUMENTS 0 398 625 A2  11/1990  European Pat. Off. .
WO 96/02874  2/1996  WIPO .

OTHER PUBLICATIONS

"Probe Type Oxygen Analyzer Package With Digital Electronics", Rosemount Analytical Inc. Instruction Bulletin IB–106–101U, Model 218 (Jun. 1989), p. 1–1 to 8–5.

"7875—In–Situ Zirconium Oxygen Analzyer", Early version of manual by Leeds & Northrup (1979).

"Something Extra in Performance, In–Situ Zirconia Oxygen Analyzer", Advertising Sheet by Leeds & Northrup (1979).

Model 132 Oxygen Analyzer Package with Digital Electronics, Instruction Bulletin IB–106–106A (Jun. 1989) Rev. 6, by Rosemount Analytical Inc.

"7875 In–Situ Zirconia Oxygen Analyzer", Manual 277141 Rev. A1, by Leeds & Northrup (1979).

"Oxygen Analyzer Package with Analog Electronics (FM Approved)", Descriptive Bulletin 106–101, by Rosemount Analytical Inc., (Jul. 1990) pp. 1–4.

"World Class 3000 Oxygen Analyzer Package", Descriptive Bulletin 106–300, by Rosemount Analytical Inc., (Jul. 1990) pp. 1–6.

"Mini Probe Oxygen Analyzer with Digital Electronics Package, for Small Packaged Boilers", Descriptive Bulletin 106–106A, by Rosemount Analytical Inc., Sep. 1989, pp. 1–4.

"Hagan Probe Type Excess Oxygen/Excess Combustibles Analyzer", Descriptive Bulletin 106–104, by Rosemount Analytical Inc., pp. 1–4, Date unavailable.

*Primary Examiner*—T. Tung
*Attorney, Agent, or Firm*—Westman, Champlin & Kelly, P.A.

[57] ABSTRACT

A solid electrolyte gas analyzer includes an analyzer circuit housed in an electronics housing and a probe housing for immersion in the gas of interest. The electronics housing mounts directly to the probe housing, preferably through a standoff. The analyzer circuit is powered by an AC line input and includes a switching power supply to convert the AC line input to DC power useable by the analyzer circuit. The analyzer circuit also includes a heater circuit controlling a heater in the probe housing. The power supply and the heater circuit automatically adjust to different AC line input voltage levels. The switching power supply efficiently supplies DC power to other portions of the analyzer circuit with little heat generation.

6 Claims, 5 Drawing Sheets

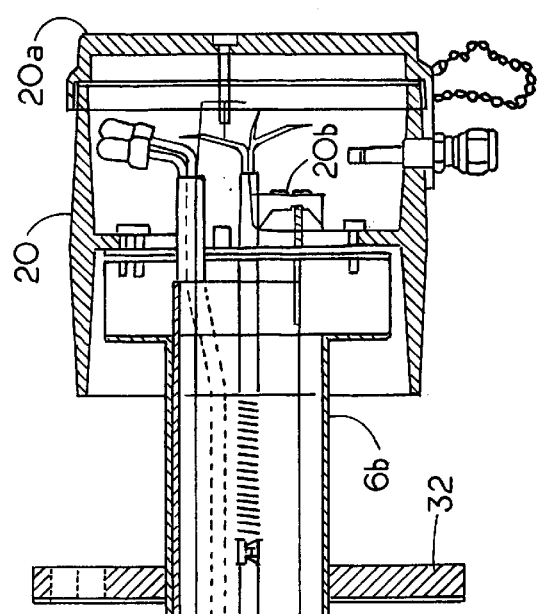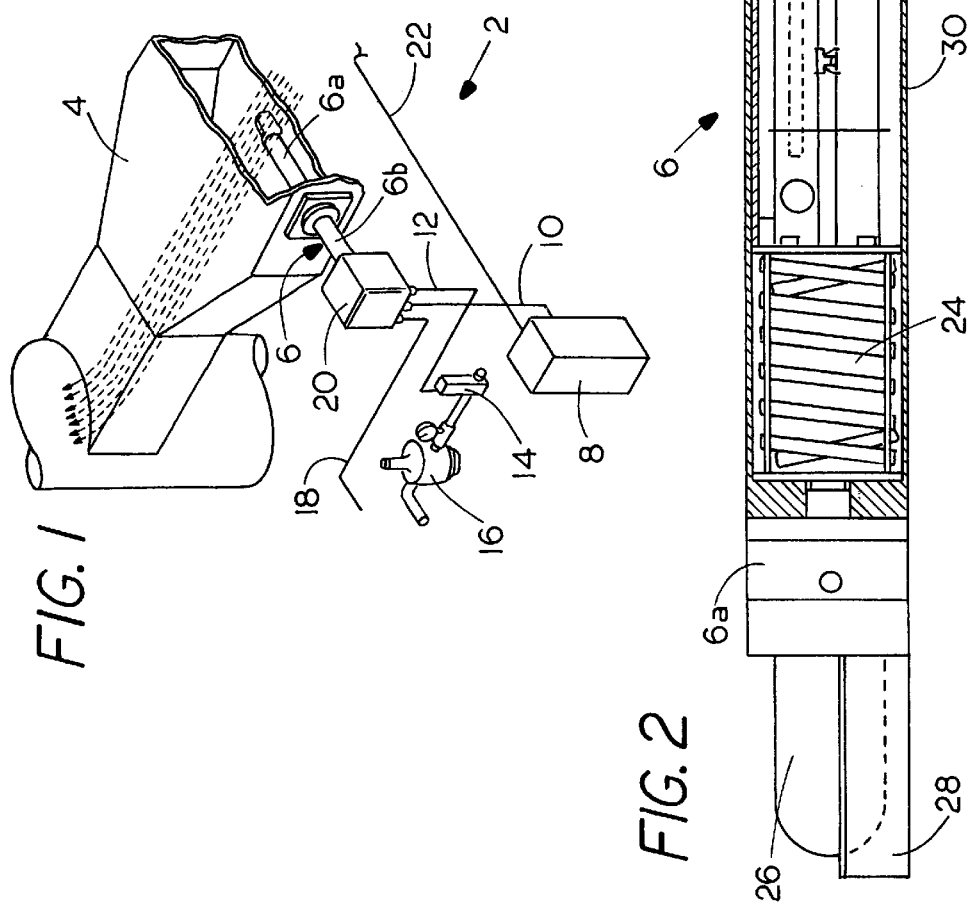

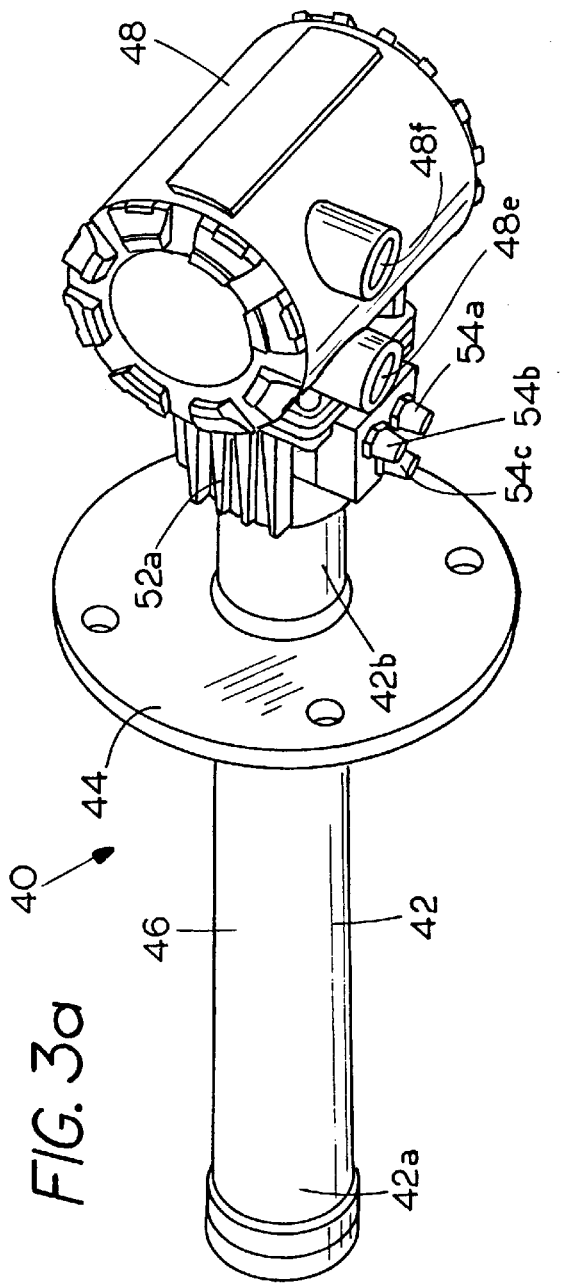
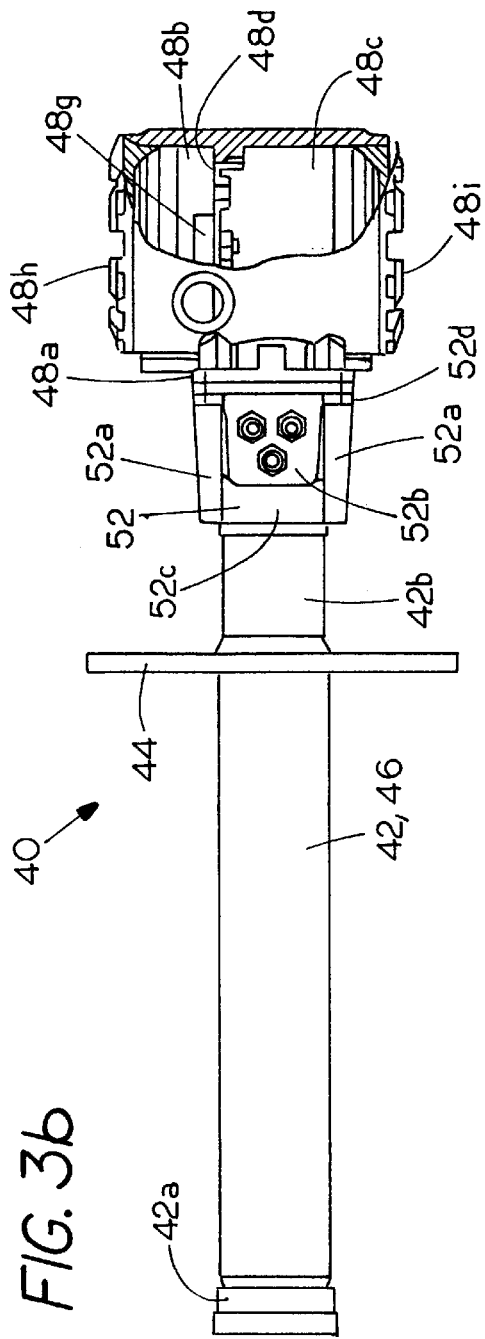
FIG. 3a
FIG. 3b

SOLID ELECTROLYTE GAS ANALYZER WITH IMPROVED CIRCUIT AND HOUSING CONFIGURATION

CROSS REFERENCE TO RELATED APPLICATIONS

This application relates to co-pending U.S. patent application entitled "Diagnostic Method and Apparatus For Solid Electrolyte Gas Analyzer", Ser. No. 08/719,140, incorporated herein by reference, assigned to the same assignee as the present application and filed on even date herewith.

BACKGROUND OF THE INVENTION

The present invention relates generally to the segment of the field of gas analysis instrumentation that involves the use of solid electrolyte cells to measure gaseous species. More specifically, the invention relates to a novel housing configuration and electronic circuitry for use with a heated solid electrolyte cell. As used herein, the term solid electrolyte cell means a quantity of the solid electrolyte, for example zirconia-yttria $((ZrO_2)_{(1-x)} (Y_2O_3)_x)$, and porous electrical contacts or electrodes connected thereto, usually made of platinum or other suitable materials.

Gas analyzers having a probe with a solid electrolyte cell to measure gaseous oxygen are well known. See, for example, U.S. Pat. Nos. 3,400,054 and 3,928,161, incorporated herein by reference. Another example is the World Class 3000 Oxygen Analyzer sold by Rosemount Analytical Inc. of Orrville, Ohio, available with replacement cells under part no. 4847B61G01/02/03. A common application for such analyzers is the measurement of gaseous oxygen in a flue or duct such as a smokestack. At a given elevated temperature, the solid electrolyte cell generates an EMF $V_{cell}$ as a function of the concentration of oxygen (or other gaseous specie) exposed to the cell. $V_{cell}$ can be approximated by the Nernst equation:

$$V_{cell} = C + S \cdot log\{P(O_2)/P(O_2)_{REF}\},$$

where C is a cell constant, S is a cell slope which is a function of cell temperature T, and $P(O_2)$ and $P(O_2)_{REF}$ are the oxygen partial pressure at a measurement and reference end, respectively, of the solid electrolyte cell. Actual solid electrolyte cells deviate from the Nernst equation to some extent.

It is also known for such analyzers to include analog or digital electronic circuitry in a housing separate from the probe that measures $V_{cell}$ and provides an analyzer output indicative of the gaseous species concentration. The probe is configured with a heater and thermocouple, controlled by circuitry in the separate housing, to maintain the solid electrolyte cell at a constant elevated temperature (e.g., 750 C.).

An object of the invention is to provide a compact, rugged, low-cost housing for a solid electrolyte gas analyzer. The housing should simplify installation and provide structural integrity for the analyzer, while maintaining the analyzer circuit at an acceptable operating temperature.

Another object of the invention is to reduce the size and heat dissipation of the analyzer circuit to permit such circuit to be housed in a compact and relatively high temperature compartment.

Still another object of the invention is to provide a heater circuit and preferably a complete analyzer circuit capable of receiving different AC line input voltages (e.g., 120 VAC and 240 VAC) and self-adjusting for such different AC inputs so as to maintain the heater and solid electrolyte cell at a specified temperature.

Other objects of the invention will become apparent from the detailed description of the invention and the accompanying drawings.

BRIEF SUMMARY OF THE INVENTION

According to one aspect of the invention, an assembly for mounting a solid electrolyte cell that provides an output as a function of a gas of interest, and an analyzer circuit therefor, includes a probe housing, an electronics housing, and the analyzer circuit. The analyzer circuit is couplable to the solid electrolyte cell and carried by the electronics housing. The probe housing has a distal end and a proximal end, the distal end being sized to carry the cell. Advantageously, the electronics housing mounts to the proximal end of the probe housing. In a preferred embodiment the assembly also includes a standoff with cooling fins connecting the electronics housing to the probe housing. In another preferred embodiment the analyzer circuit includes a switching power supply to supply DC power to portions of the analyzer circuit.

According to another aspect of the invention, an analyzer circuit for a heated solid electrolyte cell is powered by an AC line input and includes a heater circuit. The heater circuit includes a selectable circuit element having a state that is controlled automatically by the analyzer circuit as a function of a voltage level of the AC line input. In a preferred embodiment the selectable circuit element is a capacitor in a delay circuit portion of the heater circuit, and the analyzer circuit decouples the capacitor from the heater circuit for low voltage AC line inputs and couples the capacitor for high voltage AC line inputs.

According to still another aspect of the invention, an apparatus measuring a gas constituent in a gas of interest includes a probe adapted for immersion in the gas of interest and an analyzer circuit coupled to the probe. The analyzer circuit includes a power supply receiving an AC line input and providing a DC output to other portions of the analyzer circuit. The power supply includes a transformer having a primary winding and a secondary winding, and a switching regulator coupled to the primary winding. The DC output is provided over the secondary winding. Preferably, the switching regulator couples in series to the primary winding and switches at a frequency greater than about 50 kHz.

BRIEF DESCRIPTION OF THE DRAWINGS

FIG. 1 shows a PRIOR ART gas analyzer setup with the analyzer probe installed in a duct or flue.

FIG. 2 is an elevational view partially in section of a PRIOR ART gas analyzer probe.

FIGS. 3a and 3b are perspective and elevational views, respectively, of a gas analyzer of the present invention, with the view of FIG. 3b being partially broken away.

Figure 4:
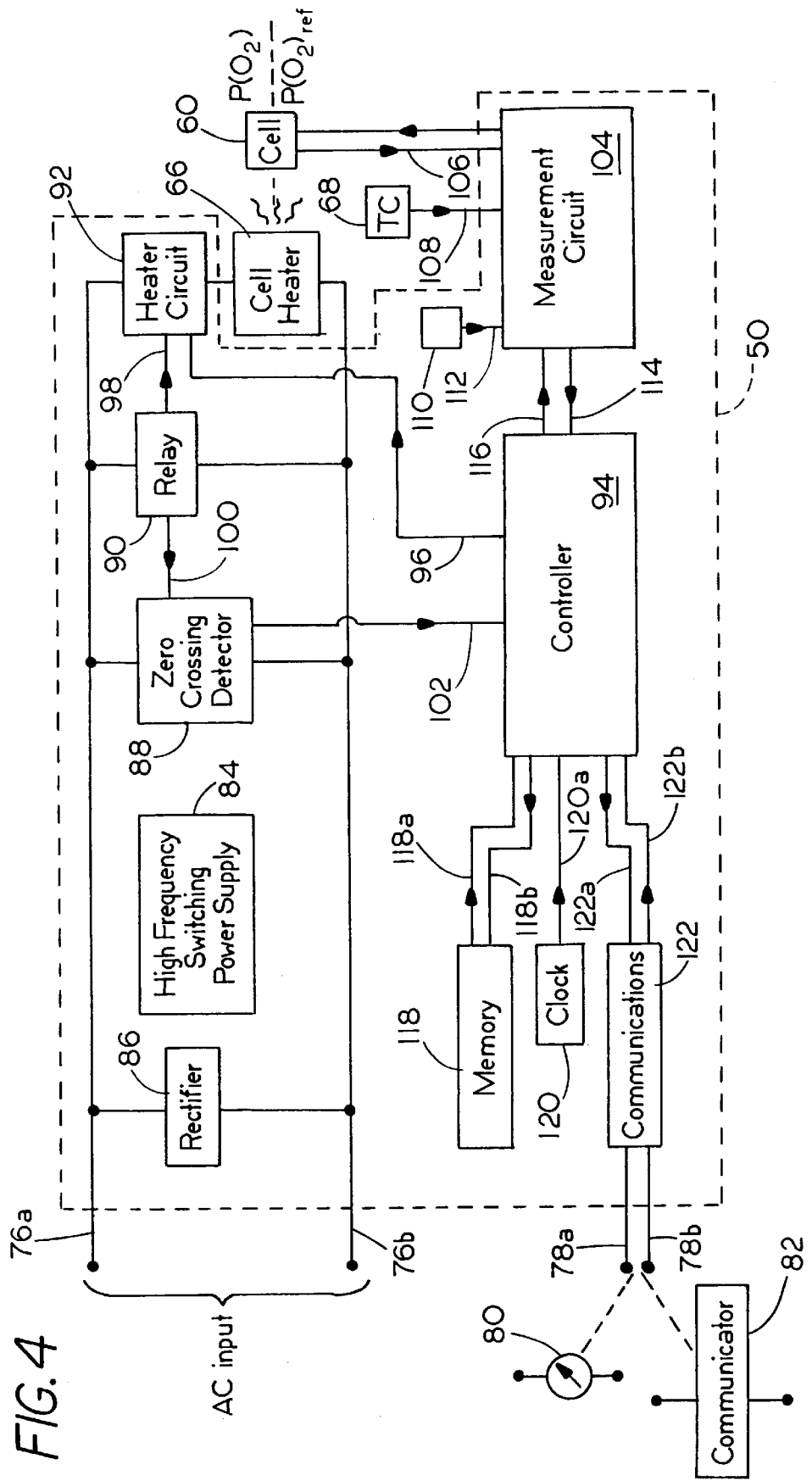
FIG. 4 is a block diagrammatic schematic of analyzer circuitry of a preferred embodiment.

For convenience, items in the figures having the same reference symbol are the same or serve the same or a similar function.

DETAILED DESCRIPTION OF THE PREFERRED EMBODIMENTS

In FIG. 1, a PRIOR ART solid electrolyte gas analyzer 2 is installed in a flue or duct 4 and measures a gas of interest in the duct. Analyzer 2 includes an analyzer probe 6 having a distal end 6a which inserts into the duct and a proximal end 6b which extends out of the duct. Duct 4 and its immediate vicinity can reach temperatures unsuitable for many electronic components. Therefore, analyzer 2 also includes an electronics package 8 mounted in a separate (cooler) location from the probe and connected thereto by an electrical cable 10. A solid electrolyte cell (not shown in FIG. 1) mounts in the distal end 6a of probe 6 with one side of the cell exposed to duct air and another side exposed to reference air. The cell generates an output $V_{cell}$ as a function of the temperature of the cell and of the difference in partial pressure of oxygen ($P(O_2)$) between the two sides of the cell. Reference gas is continuously supplied to the probe 6 by a pneumatic line 12 using a flow controller 14 and a pressure regulator 16. Another pneumatic line 18 leads to the side of the cell exposed to duct air and is normally closed except during a calibration procedure, when gasses of known $P(O_2)$ are sequentially pumped through line 18 to expose the duct air side of the cell to the known calibration gasses.

The PRIOR ART analyzer 2 includes a junction box 20 at the proximal end 6b of the probe 6. Junction box 20 includes fittings for pneumatic lines 12,18 and a terminal block to connect wires from electrical cable 10 to corresponding wires running along the interior of probe 6. Cable 10 carries electrical power from electronics package 8 to a cell heater inside probe 6, and transmits the cell output $V_{cell}$ and a thermocouple output from probe 6 to package 8. Although cable 10 includes electrical shielding, the signals it transmits (particularly the low level signals from the cell and thermocouple) are nevertheless subject to EMI noise and degradation. Electronics package 8 provides an analyzer output indicative of the duct air $P(O_2)$ to a remote site (not shown) on a cable 22 in a 4–20 mA format or other standard format. The remote site also powers package 8 with AC line input over cable 22.

An elevational view, partially in section, of the PRIOR ART analyzer probe 6 of FIG. 1 is shown in FIG. 2. The solid electrolyte cell is disposed inside a cell heater 24 at distal end 6a. A thermocouple is disposed proximate heater 24. The probe includes a ceramic filter 26 to prevent particulate matter from contacting the cell while permitting passage of oxygen. A shield 28 protects filter 26 from damage due to debris entrained in the flue gas. A tubular member 30 holds the cell heater 24 and cell at one end and the junction box 20 connects to the other end by screws. Junction box 20 includes an access door 20a, terminal block 20b, and ports for pneumatic tubing access and electrical wiring access. A mounting flange 32 connected to tubular member 30 defines the placement of the probe 6 on the wall of a flue.

A solid electrolyte analyzer 40 constructed in accordance with one aspect of the present invention is shown in FIGS. 3a and 3b. Analyzer 40 comprises an analyzer probe 42 having a distal end 42a, a proximal end 42b, and a mounting flange 44 affixed therebetween to a tubular member 46. Analyzer circuit 50 (see FIG. 4) is housed in a can 48 that mounts to the probe 42 at the proximal end 42b through a standoff 52. The result is a combined analyzer/probe having reduced installation costs compared to present day analyzers which require a separate mounting site for the analyzer circuit and an interconnecting cable. Further, corruption of the outputs from the cell and thermocouple (both mounted in distal end 42a) is minimized by keeping the length of the interconnecting wires short and shielding them with the analyzer housing comprising the tubular member 46, can 48, and standoff 52, all of which are preferably metallic.

Standoff 52 helps the analyzer circuit 50 survive the high temperatures near the flue by distancing electronics can 48 from the flue. Standoff 52 also functions as a heat sink between tubular member 46 and can 48 by virtue of cooling fins or ridges 52a on its outer surfaces to dissipate heat to surrounding ambient air. The wall thickness of tubular member 46 is reduced between flange 44 and standoff 52 to reduce heat conduction along the tubular member. The wall thickness can be reduced by removing material from the outside diameter of tube 46 as shown in FIG. 3b or from the inside diameter or both.

Standoff 52 has a face 52b that carries pneumatic fittings 54a,54b,54c used for the introduction of reference gas, calibration gas and for a vent. By placing fittings 54a,54b, 54c on standoff 52, the pneumatic and electrical connections are divided between standoff 52 and electrical can 48. This separation simplifies operation and serviceability of analyzer 40 by permitting pneumatic connections to be serviced independently of the electrical connections and vice versa. Standoff 52 has a round end 52c and a square end 52d to adapt a square base 48a of can 48 to the tubular member 46 which is round.

Electronics can 48 is preferably divided into two chambers 48b,48c by a wall 48d. Ports 48e,48f open to chamber 48b and preferably face in the same direction as pneumatic fittings 54a,54b,54c. Both are preferably oriented downward to avoid accumulation of water or other liquids. Chamber 48b holds a terminal block 48g, which communicates with analyzer circuit 50 disposed in chamber 48c by electrical feedthroughs in wall 48d. Screw-on covers 48h,48i permit access to chambers 48b,48c, respectively.

FIG. 4 shows a block diagram of the preferred analyzer circuit 50. Circuit 50 is energized by AC line input provided across lines 76a,76b by a remote source that couples to electronics can 48 via one of ports 48e,48f. Circuit 50 controls a cell heater 66, monitors the cell output $V_{cell}$ from a solid electrolyte cell 60 and the cell/heater temperature T from a thermocouple 68, and communicates a parameter indicative of $P(O_2)$ over lines 78a,78b to a meter 80 or communicator 82 which can also be remote from electronics can 48. Communicator 82 can also send commands and other signals to circuit 50, preferably using HART® or fieldbus protocol over lines 78a,78b.

To provide low voltage DC power to its various circuit components, circuit 50 uses a switching power supply 84 coupled to lines 76a,76b through a rectifier 86. Use of switching power supply 84 rather than a standard transformer-rectifier circuit increases AC to DC conversion efficiency, resulting in substantially reduced heat dissipation. This is particularly advantageous where the electronics can 48 mounts to the analyzer probe 42 (with or without standoff 52), with overheating of the analyzer electronics being a concern. Switching power supply 84 operating at high switching speeds, preferably above about 50 kHz, permits the use of a transformer with a greatly reduced size and weight compared to transformers designed for typical line frequencies of 50 to 60 Hz. Switching power supply 84 further is self-adjusting to AC line input voltage. I.e., power supply 84 supplies the same low voltage DC power whether the line voltage is low (e.g., 85–120 VAC) or high (e.g., 200–264 VAC).

Also coupled across lines 76a,76b in parallel with rectifier 86 are a zero crossing detector 88, a relay 90, and a series combination of a heater circuit 92 with the cell heater 66. A controller 94 turns heater circuit 92 on or off over line 96 according to a proportional-integral-derivative (PID) or other suitable algorithm to maintain thermocouple 68 at a specified temperature. According to an aspect of the invention the heater circuit 92, like the power supply circuit, self-adjusts to the AC line input used. Relay 90 controls a selectable circuit component in heater circuit 92 over a line 98 in response to the AC voltage level. The single analyzer circuit 50 is thereby useable with different AC line input voltages, resulting in reduced inventory for end users working with multiple line voltages, and reduced cost for the manufacturer by reducing overall part count and simplifying ordering.

The relay 90 can also control an impedance of the zero crossing detector 88 over a line 100 in response to the AC voltage level. Zero crossing detector 88 communicates zero crossings of the AC line input to controller 94 over line 102. Controller 94 uses such zero crossing signals to control heater circuit 92 such that positive and negative current is applied equally to cell heater 66. The resulting zero net DC current minimizes degradation of cell heater 66 caused by electroplating.

Analyzer circuit 50 further includes a measurement circuit 104 which receives the output of cell 60 over a line 106, thermocouple 68 over a line 108, and a local temperature sensor 110 monitoring the temperature inside can 48 over a line 112. These outputs are communicated to controller 94 over a line 114. Controller 94 uses the sensor 110 output as an indication of cold junction temperature to correct the raw EMF output from thermocouple 68 in calculating cell temperature T. Controller 94 can preferably command measurement circuit 104 over a line 116 to perform a diagnostic check of cell 60 over line 106a while the cell 60 is in situ, i.e., fully installed in the flue and exposed to flue gas. The diagnostic check preferably measures the impedance Z of cell 60 at one or more selected frequencies, and this value is communicated to controller 94 over line 114. For details on the diagnostic method and apparatus see the co-pending application entitled "Diagnostic Method and Apparatus For Solid Electrolyte Gas Analyzer", Ser. No. 08/719,140, filed Sep. 24, 1996, and referenced above.

Controller 94 communicates with a non-volatile memory circuit 118, a clock circuit 120, and a communications circuit 122 over lines 118a,118b, a line 120a, and lines 122a,122b respectively. Memory 118 holds information relating the measured cell output $V_{cell}$ and temperature T to a predicted oxygen content $P(O_2)$, such as the Nernst equation, as well as preferably certain diagnostic information. The controller 94 regularly monitors cell output and temperature and relays the calculated $P(O_2)$ as an analyzer output over lines 78a,78b.

Figure 5:
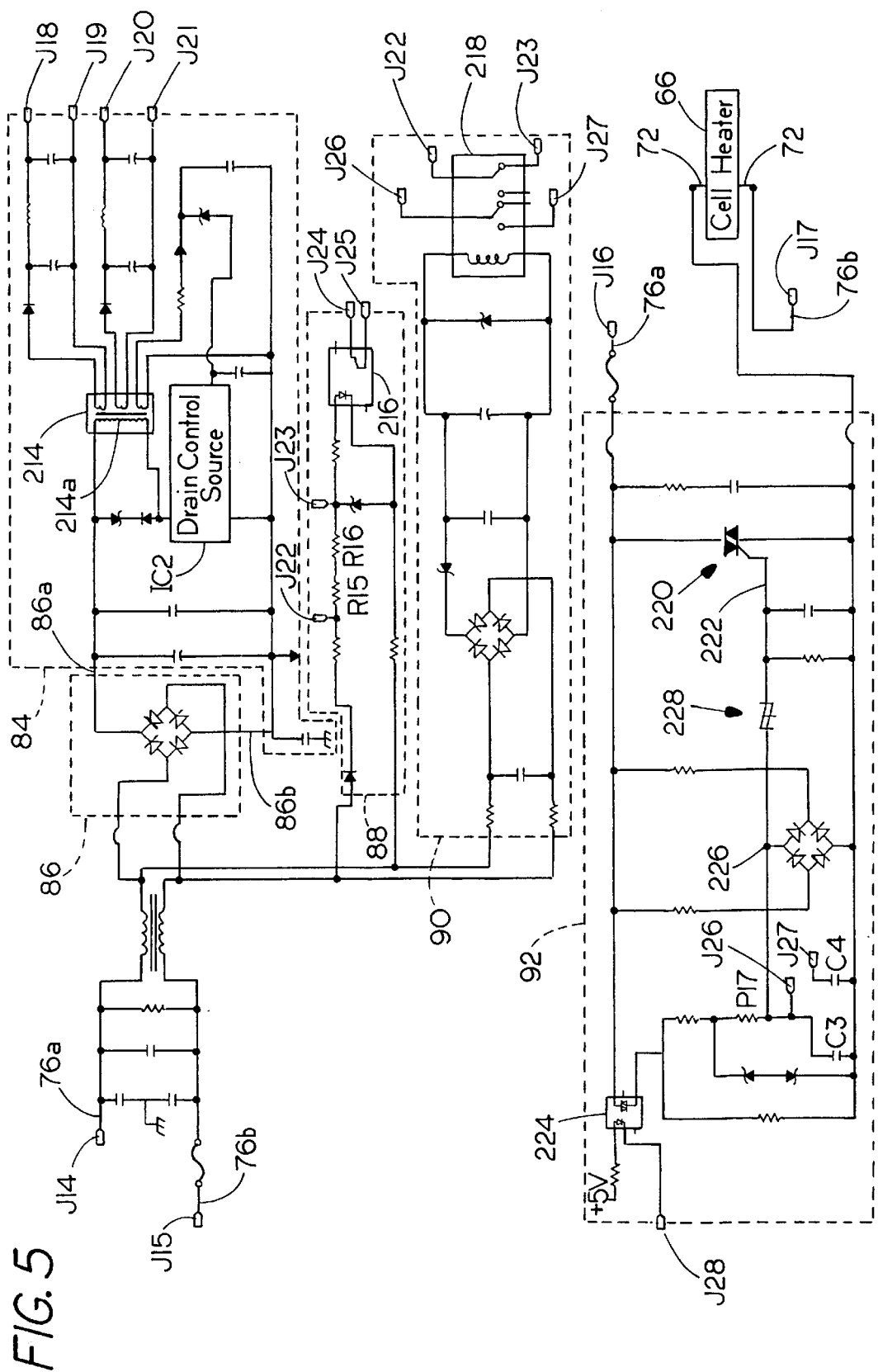
FIG. 5 is a schematic of a preferred embodiment of analyzer circuitry including a high efficiency switching power supply and a self-adjusting cell heater circuit.

Turning now to FIG. 5, preferred embodiments of previously described rectifier 86, switching power supply 84, zero crossing detector 88, relay 90, and heater circuit 92 are shown. AC line input from a source external to transmitter 40 couples across jumpers J14,J15 and across jumpers J16,J17. Rectifier 86 connects across lines 76a,76b and comprises 4 diodes connected in the usual way. Switching power supply circuit 84 couples to rectifier 86 over lines 86a,86b. Circuit 84 includes a switching regulator IC2, preferably model TOP200 available from Power Integrations, Inc., Mountain View, Calif. IC2 has a SOURCE, DRAIN, and CONTROL connection as shown and includes a variable duty cycle 100 kHz internal oscillator and an internal voltage reference. Switching regulator IC2 connects the SOURCE connection to the DRAIN connection in rapid bursts at its internal oscillator frequency, and automatically regulates the duty cycle of such bursts as needed until an input at the CONTROL connection matches IC2's internal voltage reference. By coupling the DRAIN connection to a primary winding 214a of a transformer 214 and coupling the CONTROL connection to a secondary winding of transformer 214 as shown in FIG. 13, the result is a switching power supply circuit 84 that self-adjusts for different AC line input voltages. Preferably transformer 214 has at least two and more preferably three secondary windings, one of which is used exclusively for the switching regulator feedback loop at the CONTROL connection and the other two which can provide isolated DC voltage levels to power other circuit components via jumpers J18,J19 and J20,J21. Due to the high frequency operation of switching regulator IC2, i.e., frequencies above about 1 kHz and preferably above 50 kHz, transformer 214 can be much more compact and less massive than transformers optimized for low frequency operation below about 200 Hz. Further, increased efficiencies are achieved at the higher frequencies so that less heat is generated by analyzer circuit 50 compared with known analyzer circuits that use standard AC-to-DC power supplies operating at line frequencies of 50–60 Hz. The reduced size, reduced weight, and reduced heating of analyzer circuit 50 all facilitate the combined analyzer/probe configuration of FIGS. 3a and 3b by allowing a relatively small electronics can or housing 48 mounted at a relatively high temperature location to hold the analyzer electronics 50.

Zero crossing detector 88 also connects across lines 76a,76b as shown in FIG. 5. The impedance of detector 88 can be adjusted by selectively shunting resistors R15,R16 and the opposite to prevent damage to an optoisolator 216. Shunting is accomplished by jumpers J22,J23 which connect to corresponding jumpers at a relay device 218. Jumpers J24,J25 convey a zero crossing detector output to controller 94. The output on J24,J25 transitions between shunted and open circuit at every zero voltage crossing of the AC line input on lines 76a,76b.

Relay 90 also connects across lines 76a,76b as shown in FIG. 5. The circuit elements shown are selected such that an AC line input greater than a threshold voltage level causes relay device 218 to shunt jumpers J26,J27 and isolate jumpers J22,J23. For an AC line input less than the threshold level, relay device 218 relaxes to its default condition where jumpers J26,J27 are isolated and jumpers J22,J23 are shunted. Preferably the threshold level is between the widely used line voltages of 120 VAC and 240 VAC. Jumpers J26,J27 connect to corresponding jumpers in heater circuit 92.

Heater circuit 92 connects in series to cell heater 66 across the AC line input on jumpers J16,J17. Heater circuit 92 conducts an AC current from the AC line input through cell heater 66 and through a heater control triac 220, which is controlled by a gate current in line 222. Such gate current, and triac 220, are disabled when a control signal from controller 94 on a jumper J28 goes HI, thereby causing an optoisolated triac driver 224 to become nonconducting. Preferably, controller 94 uses the output from zero crossing detector 88 to generate a signal over jumper J28 that enables heater circuit 92 only during an integer number of full cycles of the AC line input. Such control, combined with making triac 220 conduct offsetting currents for consecutive half cycles, ensures no net current flow through cell heater 66, thereby avoiding electroplating problems associated with DC control of solid electrolyte cell heaters. When controller 94 causes triac driver 224 to conduct, a first timing capacitor C3 charges through a series resistor R17 during a first AC half-cycle. After a delay time $\tau_1$ governed by R17·C3, the potential at a node 226 is sufficiently high to cause a silicon bilateral switch 228 to conduct current along line 222, thereby activating triac 220 and energizing cell heater 66 for the remainder of the first AC half-cycle at the end of which the polarity changes and bilateral switch 228 becomes nonconducting. During the next AC half-cycle timing capacitor C3 again charges through resistor R17 and after the delay time $\tau_1$ again causes bilateral switch 228 to conduct for the remainder of the second half-cycle.

According to an aspect of the invention heater circuit 92 includes a selectable circuit element such as a second timing capacitor C4 that couples in parallel with capacitor C3 via jumpers J26,J27 controlled by relay device 218 in response to the AC line input voltage. Thus for a line input of 120 VAC, relay device 218 is in its default condition, C4 is isolated from C3, and delay time $\tau_1$ applies for both half-cycles. For a higher line input of 240 VAC, relay device 218 is activated, C4 is in parallel with C3, and a longer delay time $\tau_2$ governed by R17·(C3+C4) applies for both half-cycles.

Figure 6A:
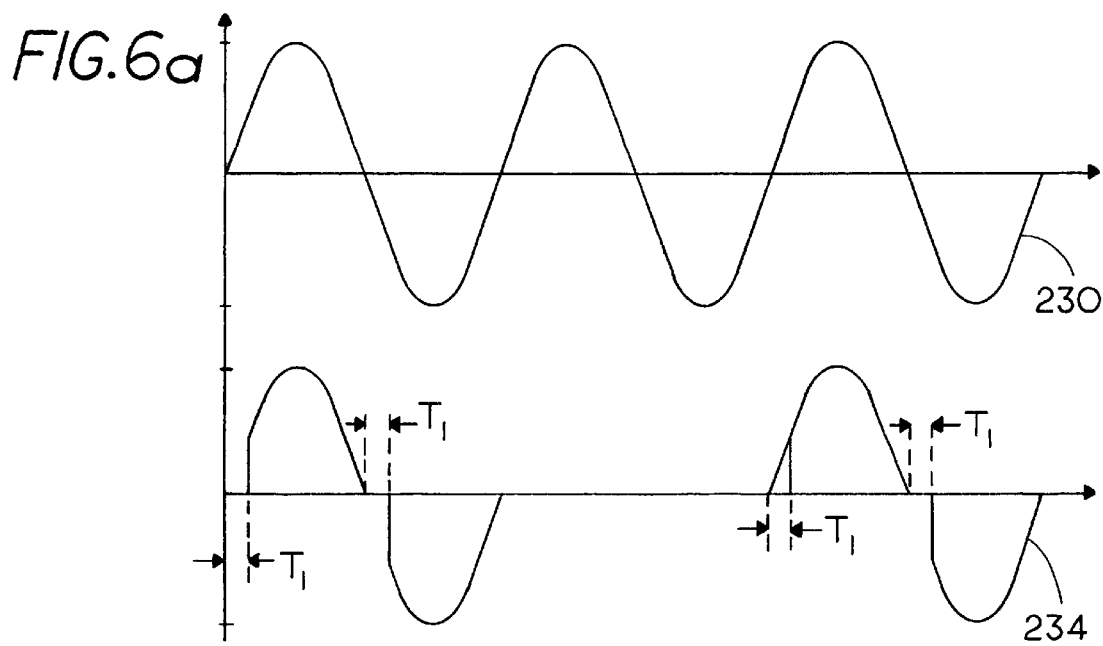
FIGS. 6a and 6b are waveforms associated with the heater circuit of FIG. 5.
Figure 6B:
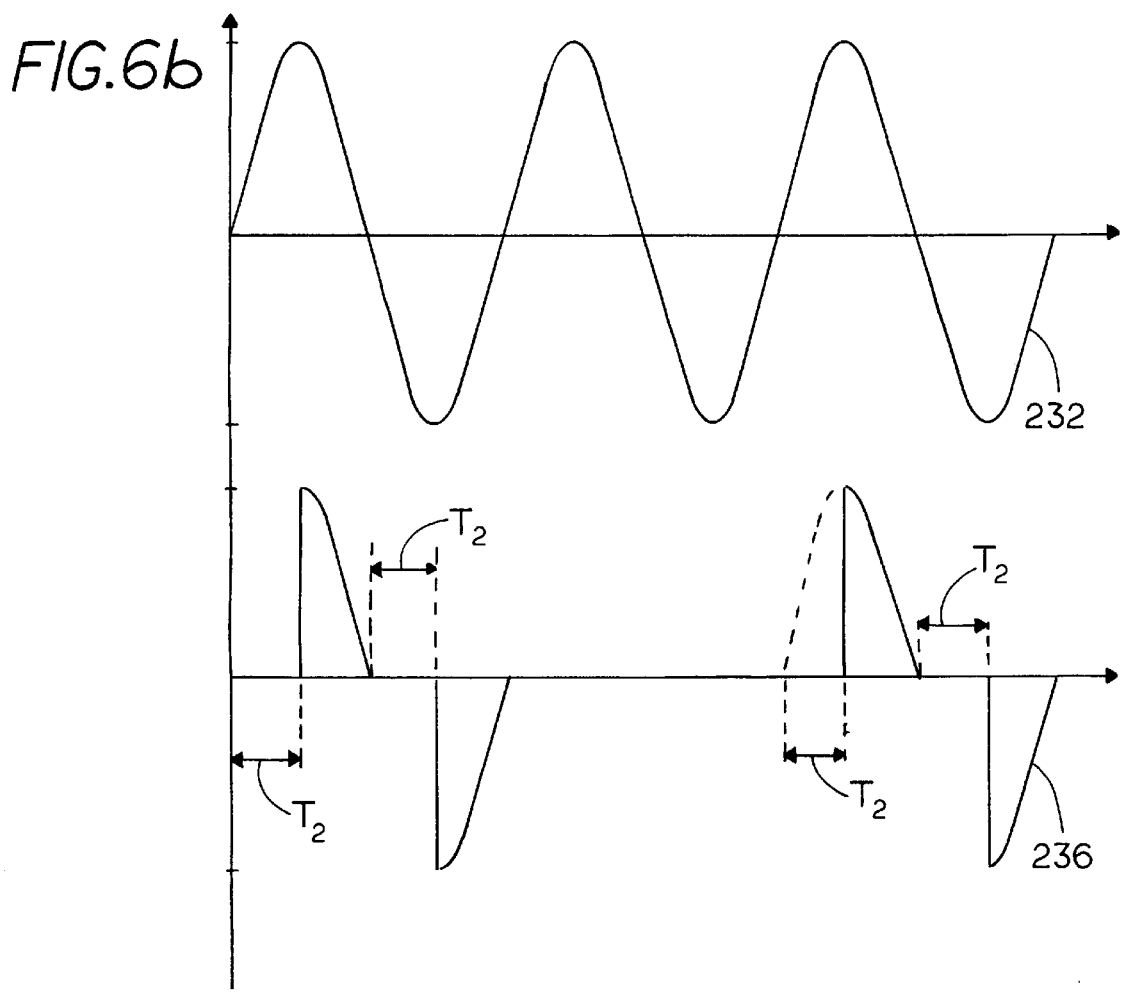

The voltage-versus-time waveforms of FIGS. 6a and 6b aid in understanding heater circuit 92. In FIG. 6a a low voltage AC line input such as 85–120 VAC, 60 Hz is used and relay 90 is not activated. In FIG. 6b a high voltage AC line input such as ~240 VAC, 60 Hz is used and relay 90 is activated. Waveforms 230 and 232 represent the AC line input across jumpers J16,J17 (as well as across J14,J15). Waveforms 234 and 236 represent the voltage across cell heater 66 for the low and high voltage AC inputs, respectively. Cell heater 66 typically has an impedance between about 70 and 80 Ω. For the waveforms illustrated, controller 94 activates heater circuit 92 for the first and third but not the second full AC cycle. For each activated full cycle, heater circuit 92 applies AC line input to cell heater 66 after a predetermined delay for both half-cycles. I.e., truncated AC half-cycle signals are applied to cell heater 66. The truncation or delay is greater for the higher AC input than for the lower AC input. Preferably, the delays $\tau_1$ and $\tau_2$ are selected such that the RMS power in a full cycle of waveform 234 is the same as the RMS power in a full cycle of waveform 236. Such selection of $\tau 1$ and $\tau 2$ results in consistent, stable temperature control at both high and low AC line voltages.

Although the present invention has been described with reference to preferred embodiments, workers skilled in the art will recognize that changes can be made in form and detail without departing from the spirit and scope of the invention as defined by the claims appended hereto. The invention pertains to solid electrolyte gas analyzers but does not encompass the solid electrolyte cell itself, which can have various configurations and compositions.

What is claimed is:

1. An apparatus to measure a gas constituent in a gas of interest, the apparatus including a probe adapted for immersion in the gas of interest, the apparatus comprising:
    an analyzer circuit coupled to the probe and providing an analyzer output indicative of an amount of the gas constituent, the analyzer circuit including a power supply receiving an AC line input and providing a DC output to other portions of the analyzer circuit, the power supply including:
        a transformer having a primary winding and a first secondary winding; and
        a switching regulator coupled to the primary winding;
    wherein the power supply provides the DC output over the first secondary winding.

2. The apparatus of claim 1, wherein the transformer further has a second secondary winding, wherein the switching regulator has a control input coupled to the second secondary winding, and wherein the switching regulator controls current through the primary winding such that the DC output is maintained at a DC setpoint for a range of AC voltage levels of the AC line input.

3. The apparatus of claim 2, further including a heater disposed in the probe and wherein the analyzer circuit further includes:
    a heater circuit coupled to the heater to control the heater, the heater circuit having a self-adjustment capability to adapt the heater circuit to at least a first and second AC voltage level within the range of AC voltage levels;
    whereby the apparatus is operable at both the first and second AC voltage levels.

4. The apparatus of claim 1, wherein the probe has a distal end and a proximal end, the distal end being adapted for immersion in the gas of interest, the apparatus further comprising:
    an electronics housing mounted to the proximal end and carrying the analyzer electronics.

5. The apparatus of claim 1, wherein the switching regulator couples in series to the primary winding and switches at a frequency greater than about 1 kHz.

6. The apparatus of claim 1, further including a heater disposed in the probe and wherein the analyzer circuit further includes:
    a heater circuit coupled to the heater to control the heater, the heater circuit having a self-adjustment capability to adapt the heater circuit to AC line inputs of different voltage levels.

* * * * *